US012690809B2

(12) United States Patent
Svanegaard et al.

(10) Patent No.: US 12,690,809 B2
(45) Date of Patent: Jul. 28, 2026

(54) MEDICAL SYSTEM, SERVER DEVICE, AND ACCESSORY DEVICE FOR MEDICAL APPLIANCE BASE PLATE MONITORING

(71) Applicant: Coloplast A/S, Humlebaek (DK)

(72) Inventors: Mads Hindhede Svanegaard, Bagsvaerd (DK); Esben Stroebech, Hoersholm (DK); Jacob Eisenberg, Greve (DK); Carsten Hellum Olsen, Frederiksberg (DK); Jeppe Malmberg, Copenhagen V (DK); Alex Poulsen, Vaerloese (DK)

(73) Assignee: Coloplast A/S, Humlebaek (DK)

( * ) Notice: Subject to any disclaimer, the term of this patent is extended or adjusted under 35 U.S.C. 154(b) by 1049 days.

(21) Appl. No.: 16/979,528

(22) PCT Filed: Feb. 20, 2019

(86) PCT No.: PCT/DK2019/050060
§ 371 (c)(1),
(2) Date: Sep. 10, 2020

(87) PCT Pub. No.: WO2019/174687
PCT Pub. Date: Sep. 19, 2019

(65) Prior Publication Data
US 2021/0000414 A1 Jan. 7, 2021

(30) Foreign Application Priority Data
Mar. 15, 2018 (DK) ........................... PA 2018 70162

(51) Int. Cl.
*A61B 5/00* (2006.01)
*A61F 5/44* (2006.01)
(Continued)

(52) U.S. Cl.
CPC .......... *A61B 5/4851* (2013.01); *A61B 5/0002* (2013.01); *A61B 5/6833* (2013.01); (Continued)

(58) Field of Classification Search
CPC ... A61B 5/4851; A61B 5/0002; A61B 5/6833; A61B 5/72; A61B 5/0404; A61B 5/332; (Continued)

(56) References Cited

U.S. PATENT DOCUMENTS

2013/0324952 A1    12/2013    Krystek et al.
2017/0140103 A1*   5/2017    Angelides ............. A61F 5/4404
(Continued)

FOREIGN PATENT DOCUMENTS

WO    2007098762 A1    9/2007

*Primary Examiner* — Rebecca E Eisenberg
*Assistant Examiner* — Timothy L Flynn
(74) *Attorney, Agent, or Firm* — Coloplast Corp., Coloplast A/S; Nick Baumann

(57) ABSTRACT

An ostomy system, accessory device, and server device is disclosed. A server device (10) for an ostomy system (1) of a user is disclosed, the ostomy system comprising a monitor device (6), an ostomy appliance (2), and an accessory device (8), the ostomy appliance comprising a base plate (4), the server device comprising a memory; one of more processors; and an interface coupled to the one or more processors and configured to communicate with the accessory device, wherein the one or more processors are configured to obtain accessory data and associated base plate identifiers from a set of accessory devices; obtain abase plate identifier of a base plate from the accessory device; determine a first base plate parameter of the base plate based on the base plate identifier; and transmit the first base plate parameter to the accessory device.

20 Claims, 14 Drawing Sheets

(51) Int. Cl.
    *A61F 5/443*         (2006.01)
    *G16H 40/40*        (2018.01)

(52) U.S. Cl.
    CPC .............. *A61B 5/72* (2013.01); *A61F 5/4404* (2013.01); *A61F 5/443* (2013.01); *G16H 40/40* (2018.01)

(58) Field of Classification Search
    CPC .. A61F 5/44; A61F 5/445; A61F 5/443; A61F 5/4404; G16H 40/40; G16H 40/60
    See application file for complete search history.

(56)             References Cited

U.S. PATENT DOCUMENTS

2018/0059093 A1*   3/2018   Hayter ................... G01N 33/49
2019/0192072 A1*   6/2019   Bailey .................... A61F 2/389

* cited by examiner

4

211

210

290, 290A 288, 288A 292, 292A 286, 286A 282, 282A 284, 284A

MEDICAL SYSTEM, SERVER DEVICE, AND ACCESSORY DEVICE FOR MEDICAL APPLIANCE BASE PLATE MONITORING

The present disclosure relates to an ostomy system and devices thereof. The ostomy system comprises an ostomy appliance, a monitor device, an accessory device, and a server device. In particular, the present disclosure relates to a server device, and an accessory device, e.g. for monitoring and communicating an operating state of the base plate based on accessory data from a large number of users.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
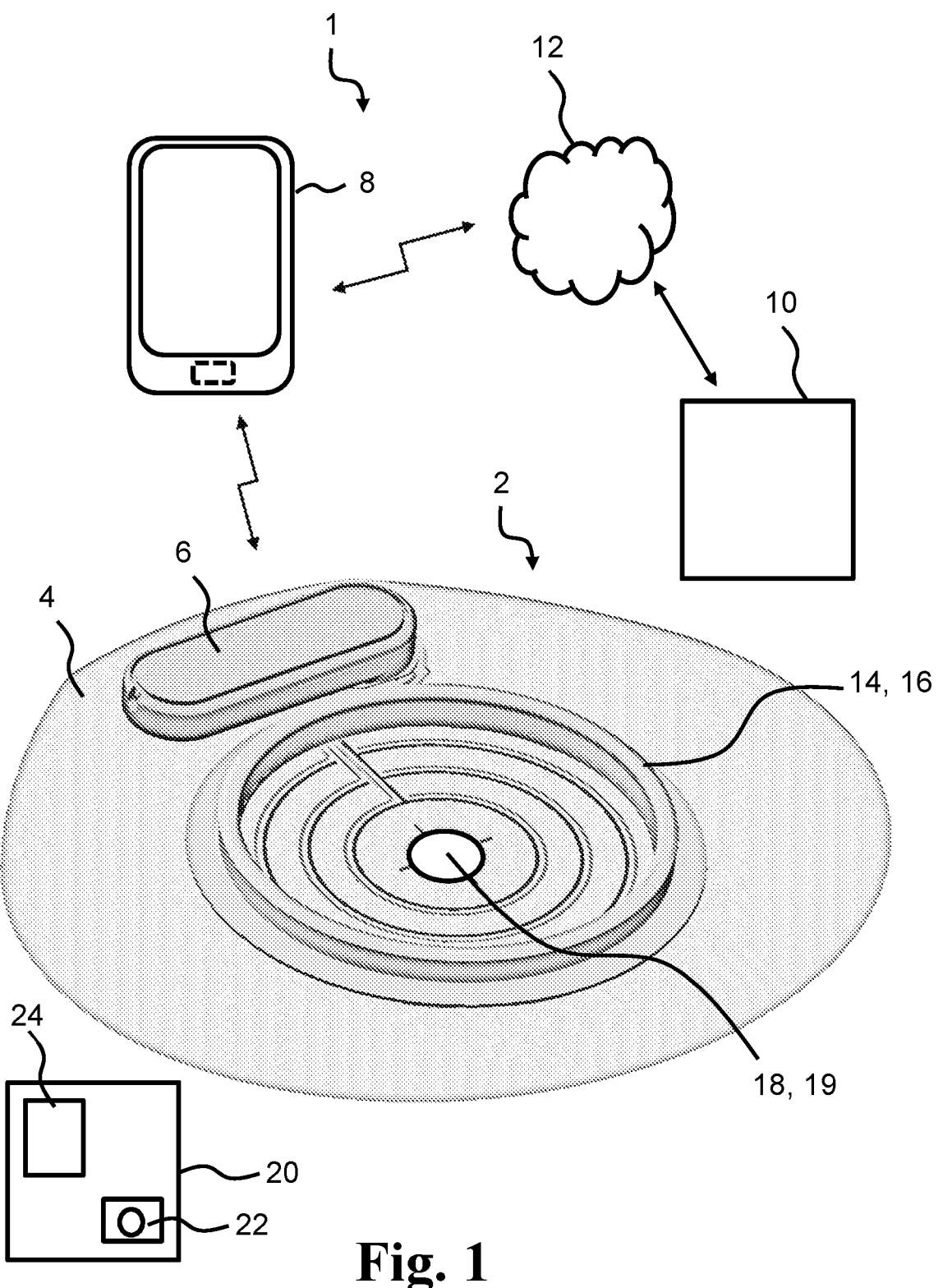
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface when a user wears the ostomy appliance/monitor device. Likewise, whenever referring to the distal side or surface of a layer, an element, a device or part of a device, the referral is to the side or surface facing away from the skin when a user wears the ostomy appliance/monitor device. In other words, the proximal side or surface is the side or surface closest to the user when the appliance is fitted on a user and the distal side is the opposite side or surface—the side or surface furthest away from the user in use.

The axial direction is defined as the direction of the stoma when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

An ostomy system comprising an ostomy appliance and a monitor device, the ostomy appliance comprising a base plate is disclosed, wherein the monitor device is a monitor device as described herein.

An ostomy system comprising a monitor device and an ostomy appliance comprising a base plate is disclosed, the base plate having a first adhesive layer with a proximal side configured for attachment of the base plate to the skin surface of a user, the first adhesive layer having a stomal opening with a center point, the monitor device comprising a processor and a sensor unit comprising a first sensor with a first sensor surface accommodated in a monitor device housing, the monitor device housing having a sensor opening in a proximal surface of the monitor device, the sensor opening forming at least a part of a sensor path from surroundings of the proximal surface to the first sensor surface.

Also disclosed is a monitor device for an ostomy appliance of an ostomy system, the monitor device comprising a processor and a sensor unit comprising a first sensor with a first sensor surface accommodated in a monitor device housing, the monitor device housing having a sensor opening in a proximal surface of the monitor device, the proximal surface configured for facing the skin of a user during use, the sensor opening forming at least a part of a sensor path from surroundings of the proximal surface to the first sensor surface.

The present disclosure provides an ostomy system and devices thereof, such as an ostomy appliance, a base plate for an ostomy appliance, a monitor device, an accessory device, and a server device which either alone or together may facilitate reliable monitoring of the ostomy appliance.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. due to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

A base plate for an ostomy appliance is disclosed, the base plate comprising a first adhesive layer with a proximal side configured for attachment of the base plate to the skin surface of a user, the first adhesive layer having a stomal opening with a center point; and a plurality of electrodes including a ground electrode, a first electrode, and a optionally a second electrode, the ground electrode comprising a ground connection part, the first electrode comprising a first connection part, and the second electrode comprising a second connection part, wherein the ground electrode forms a ground for the first electrode and/or the second electrode.

The base plate comprises a first adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer has a stomal opening with a center point or is at least prepared for forming a stomal opening with a center point. A base plate with three electrodes having sensing parts with contact to the first adhesive layer allows for determining erosion/swelling properties or characteristics of the first adhesive layer and/or determining a degree of erosion and/or swelling of the first adhesive layer.

It is an advantage of the present disclosure that an optimum or improved use of an ostomy appliance is provided. In particular, the present disclosure facilitates that a base plate is not changed too early (leading to increased cell-stripping from the skin and increased risk of skin damage and further leading to increased costs and/or material waste) nor too late (leading to adhesive failure, leakage and/or skin damage from the aggressive output). Accordingly, the user or a health care professional is able to monitor and plan the use of the ostomy appliance.

Further, determination of operating state and classification of operating states of the ostomy appliance is useful in helping to reduce the risk of a user experiencing leakage from an ostomy appliance. Further, determination of operating state and classification of operating states of the ostomy appliance is further useful in helping reduce the risk of skin damage to a user. In particular, determination of operating state according to the present disclosure may help provide a clear distinction or differentiation between adhesive failure, leakage of output, which is harmful to the skin, and a sweating ostomate.

The present disclosure provides a simple, efficient, and easy-to-use ostomy appliance system with a high degree of comfort for a user.

The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The first adhesive layer may have a plurality of sensor point openings. A sensor point opening of the first adhesive layer is configured to overlap a (sensing) part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap (sensing) parts of an electrode and the primary second sensor point openings configured to overlap (sensing) parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap (sensing) parts of an electrode and the secondary second sensor point openings configured to overlap (sensing) parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap (sensing) parts of an electrode and the tertiary second sensor point openings configured to overlap (sensing) parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less moldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals/terminal elements. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode. The base plate, e.g. the electrode assembly, may comprise a ground electrode. The ground electrode may comprise a first electrode part. The first electrode part of the ground electrode may form a ground or reference for the first electrode. The ground electrode may comprise a second electrode part. The second electrode part of the ground electrode may form a ground or reference for the second electrode. The ground electrode may comprise a third electrode part. The third electrode part of the ground electrode may form a ground or reference for the third electrode. The ground electrode may comprise a fourth electrode part. The fourth electrode part of the ground electrode may form a ground or reference for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The ground electrode may comprise a first electrode part and a second electrode part, the first electrode part forming the ground for the first electrode and the second electrode part forming the ground for the second electrode. The first electrode part may form a closed loop.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

An electrode may comprise a sensing part or a plurality of sensing parts, i.e. the part(s) of an electrode that are used for sensing. The first electrode may comprise a first sensing part. The first sensing part may contact the first adhesive layer and is optionally arranged at least partly annularly around the stomal opening. The first electrode may comprise a first conductor part insulated from the first adhesive layer, e.g. by a masking element arranged between the first conductor part and the first adhesive layer. The first sensing part may extend at least 270 degrees around the stomal opening, such as at least 300 degrees around the stomal opening. The first sensing part of the first electrode may be arranged at a first ground distance from the first electrode part of the ground electrode. The first ground distance may be less than 5 mm, such as less than 3 mm, e.g. about 1.0 mm.

The second electrode may comprise a second sensing part. The second sensing part may contact the first adhesive layer. The second sensing part may be arranged at least partly annularly around the stomal opening. The second sensing part may extend at least 270 degrees around the stomal opening, such as at least 300 degrees around the stomal opening. The second sensing part of the second electrode may be arranged at a second ground distance from the second electrode part of the ground electrode. The second ground distance may be less than 5 mm, such as less than 3 mm, e.g. about 1.0 mm.

The first sensing part may be arranged at a first radial distance from the center point and the second sensing part may be arranged at a second radial distance from the center point. The second radial distance may be larger than the first radial distance. The second electrode may comprise a second conductor part insulated from the first adhesive layer, e.g. by a masking element arranged between the second conductor part and the first adhesive layer. The first radial distance may vary as a function of an angular position with respect to a zero direction from the center point. The second radial distance may vary as a function of an angular position with respect to a zero direction from the center point. The zero direction may be defined as the vertical upward direction when the base plate is in its intended wearing position on an upstanding user.

The first radial distance may be in the range from 5 mm to 40 mm, such as in the range from 10 mm to 25 mm, e.g. about 14 mm. The second radial distance may be in the range from 10 mm to 50 mm, such as in the range from 10 mm to 25 mm, e.g. about 18 mm.

The base plate may comprise a third electrode comprising a third connection part. The ground electrode may form a ground for the third electrode. The ground electrode may comprise a third electrode part, the third electrode part forming the ground for the third electrode. The third electrode may comprise a third conductor part insulated from the first adhesive layer, e.g. by a masking element arranged between the third conductor part and the first adhesive layer. The third electrode may comprise a third sensing part, the third sensing part contacting the first adhesive layer. The third sensing part may be arranged at least partly annularly around the stomal opening. The third sensing part may be arranged at a third radial distance from the center point. The third radial distance may be larger than the first radial distance and/or larger than the second radial distance. The third radial distance may be in the range from 15 mm to 50 mm. such as in the range from 20 mm to 30 mm, e.g. about 26 mm. The third sensing part may extend at least 270 degrees around the stomal opening, such as at least 300 degrees around the stomal opening. The third sensing part of the third electrode may be arranged at a third ground distance from the third electrode part of the ground electrode. The third ground distance may be less than 5 mm, such as less than 3 mm, e.g. about 1.0 mm. A base plate with a ground electrode, a first electrode, a second electrode, and a third electrode allow for a failsafe base plate in case e.g. the first electrode is cut or otherwise destroyed during preparation of the base plate.

The base plate may comprise a fourth electrode comprising a fourth connection part. The ground electrode may form a ground for the fourth electrode. The ground electrode may comprise a fourth electrode part, the fourth electrode part forming the ground for the fourth electrode. The fourth electrode may comprise one or a plurality of fourth sensing parts, such as at least five fourth sensing parts. The fourth sensing parts may be distributed around the stomal opening or a center point thereof. The fourth sensing parts may be arranged at respective fourth radial distances from the center point. The fourth radial distance(s) may be larger than the third radial distance. The fourth radial distance(s) may be in the range from 25 mm to 50 mm, such as about 30 mm The base plate may comprise a fifth electrode comprising a fifth connection part. The ground electrode may form a ground for the fifth electrode. The ground electrode may comprise a fifth electrode part, the fifth electrode part forming the ground for the fifth electrode. The fifth electrode may comprise one or a plurality of fifth sensing parts, such as at least five fifth sensing parts. The fifth sensing parts may be distributed around the stomal opening or a center point thereof. The fifth sensing parts may be arranged at respective fifth radial distances from the center point. The fifth radial distance may be larger than the third radial distance. The fifth radial distance may be equal to or larger than the fourth radial distance. The fifth radial distance(s) may be in the range from 25 mm to 50 mm, such as about 30 mm.

The first electrode may form an open loop. The second electrode may form an open loop, and/or the third electrode may form an open loop. The fourth electrode may form an open loop. The fifth electrode may form an open loop. Open loop electrode(s) enables electrode arrangement in few or a single electrode layer.

The base plate may comprise a second adhesive layer, wherein the plurality of electrodes is arranged between the first adhesive layer and the second adhesive layer.

The electrode assembly may comprise a support layer, also denoted a support film. One or more electrodes may be formed, e.g. printed, on the proximal side of the support layer. One or more electrodes may be formed, e.g. printed, on the distal side of the support layer. Thus, one or more electrodes may be arranged between the support layer and the first adhesive layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a (sensing) part of the ground electrode and/or a (sensing) part of the fourth electrode. A secondary sensor point opening may overlap a (sensing) part of the fourth electrode and/or a (sensing) part of the fifth electrode. A tertiary sensor point opening may overlap a (sensing) part of the fifth electrode and/or a (sensing) part of the ground electrode.

The masking element may comprise one or more, such as a plurality of, terminal openings. A terminal opening may overlap with one or more connection parts of electrodes. In one or more exemplary base plates, each terminal opening overlaps with a single connection part of an electrode.

The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm. The top layer may have a stomal opening with a center point.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes (connection parts) of the base plate/ electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

The monitor device comprises a processor. The processor controls the operation of the monitor device including collection and processing of ostomy data from the base plate of the ostomy appliance, processing of, such as storing, sensor data from sensor unit, and generation/transmission of monitor data to accessory devices.

The monitor device comprises a memory for storing ostomy data and/or parameter data based on the ostomy data. The processor may be configured for processing and storing sensor data in the memory.

The monitor device comprises a monitor device housing optionally made of a plastic material. The monitor device housing may be an elongate housing having a first end and a second end. The monitor device housing may have a length or maximum extension along a longitudinal axis in the range from 1 cm to 10 cm. The monitor device housing may have a width or maximum extension perpendicular to the longitudinal axis in the range from 0.5 cm to 5 cm, such as from 0.8 cm to 3 cm. The monitor device housing may be curve-shaped.

The monitor device housing may have a plurality of sensor openings, e.g. a plurality of sensor openings for a sensor and/or a sensor opening for each of a plurality of sensors. The monitor device may comprise one or more sensor openings in a distal surface of the monitor device. The monitor device may comprise one or more sensor openings in a side surface of the monitor device. The monitor device may comprise one or more sensor openings in an end surface of the monitor device.

The sensor opening in the proximal surface is arranged at a sensor opening distance from the first end. The sensor opening distance, also denoted D_S, may be in the range from 0.25 L to 0.75 L, such as from 0.35 L to 0.65 L, where L is the length of the monitor device housing. The sensor opening distance may be in the range from 10 mm to 70 mm.

The monitor device housing comprises or forms a sensor path from surroundings of the proximal surface to the first sensor surface. The sensor path translates temperature and/ or humidity at the proximal surface of the monitor device/ monitor device housing to the first sensor surface. The sensor opening forms a part of the sensor path and has a cross-sectional area optionally in the range from 0.2 mm$^2$ to 10 mm$^2$. The sensor opening may be a circular sensor opening with a diameter in the range from 0.3 mm to 1.4 mm, e.g. from 0.6 mm to 1.0 mm.

The monitor device comprises a sensor unit with one or more sensors including a first sensor. The sensor unit is connected to the processor for feeding sensor data to the processor. The sensor unit may comprise a humidity sensor for provision of humidity data to the processor. Thus, the sensor data may comprise humidity data. For example, the first sensor may be a humidity sensor for provision of humidity data to the processor. Thus, the present disclosure enables humidity detection near the skin of a user and/or on the distal side of the base plate, which in turn can be used for a more accurate estimation of base plate operation state.

The sensor unit may comprise a temperature sensor for provision of temperature data to the processor. Thus, the sensor data may comprise temperature data. For example, the first sensor may be a temperature sensor for provision of temperature data to the processor. Thus, the present disclosure enables temperature detection near the skin of a user and/or on the distal side of the base plate, which in turn can be used for a more accurate estimation of base plate operation state.

The first sensor may be a combined humidity and temperature sensor for provision of humidity and temperature data to the processor.

The sensor unit of the monitor device may comprise a second sensor, e.g. an accelerometer for provision of acceleration data to the processor. The sensor unit of the monitor device may comprise a third sensor, e.g. a gyroscope for provision of gyroscope data to the processor. The sensor unit of the monitor device may comprise a fourth sensor, e.g. a magnetometer for provision of magnetometer data to the processor.

The processor is configured for processing ostomy data obtained from the base plate and generate or determine monitor data that are transmitted to an accessory device. The monitor data may comprise sensor data obtained from the sensor unit.

The monitor device comprises a first interface for connecting the monitor device to the base plate. The first interface may be arranged in the proximal surface of the monitor device housing. The first interface may be arranged within a first interface distance from the first end. The first interface distance may be less than 0.50 L, such as less than 0.4 L, where L is the length of the monitor device housing.

The monitor device may comprise a sealing element forming a seal between the first sensor and a housing part of the monitor device housing. The sealing element may be an O-ring, e.g. made of a rubber material. The sealing element may encircle the first sensor surface to expose the first sensor surface (membrane) to the sensor path while providing a closed cavity of the monitor device, the closed cavity accommodating PCB, processor, and other electronic circuitry. A glue may form the sealing element.

The ostomy system enables a reliable and accurate measurement of different parameters relevant for monitoring of the ostomy appliance. In the ostomy system, a distance between the proximal surface of the monitor device and a distal surface of the base plate, in a coupled state, is in the range from 0.2 mm to 10 mm, such as in the range from 0.5 mm to 5 mm. In the coupled state, the monitor device is attached to the base plate and arranged in its intended position during use of the ostomy system.

The monitor device comprises a first interface connected to the processor. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively. The processor may be configured to transmit monitor data, as a wireless monitor signal via the antenna and the wireless transceiver.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The accessory device comprises a memory, a processor and an interface coupled to the processor. The interface comprises a display, such as a touch-sensitive display, and a transceiver unit.

The interface of the accessory device is configured to communicate with monitor device and/or server device. The interface of the accessory device may be configured to communicate with server device via a network.

The interface of the accessory device may be configured as a monitor interface for connecting, e.g. wirelessly connecting, the accessory device to one or more monitor devices. The interface of the accessory device may comprise a transceiver unit, e.g. including an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5.

The accessory device is configured to obtain monitor data from one or more monitor devices. The accessory device may be configured to transmit accessory data, e.g. to a server device. For example, the processor of the accessory device may be configured to transmit accessory data, as a wireless accessory signal via the antenna and the wireless transceiver.

The interface of the accessory device comprises a display and a transceiver unit. The interface (transceiver unit) is configured to obtain monitor data from the monitor device coupled to the ostomy appliance. The monitor data may comprise sensor data obtained from one or more sensors in the monitor device. The monitor data may comprise ostomy data obtained from electrodes of the base plate, and/or parameter data based on ostomy data obtained from elec- trodes of the base plate.

The monitor data may be indicative of a condition or operating state of the ostomy appliance, e.g. a condition of the base plate disclosed herein. The condition of the ostomy appliance or of the base plate disclosed herein may refer to a level of a physical property of at least a part of the ostomy appliance, such as a level of moisture and/or temperature of at least a part of the base plate, such as a level of a physical property of at least a layer of the base plate, such as a level of moisture and/or temperature of at least a layer of the base plate, such as a level of a physical property of at least an adhesive layer of the base plate (e.g. a first adhesive layer proximal to the skin of the user). In one or more exemplary accessory devices, the interface is configured to obtain the monitor data by obtaining the monitor data indicative of the condition comprising a moisture level of a first adhesive layer of the base plate and/or a moisture level of a proximal side of the first adhesive layer. The moisture level may be seen as representative of a conductive path in the first adhesive layer, such as across the first adhesive layer. The monitor data comprises e.g. data representative of the mea- surement of the electrical properties of the first adhesive layer. In other words, the condition may be seen as a condition of the first adhesive layer.

A user interface refers herein to a graphical representation comprising a collection of user interface objects. A user interface comprises one or more user interface objects. A user interface may be referred to as a user interface screen.

A user interface object refers herein to a graphical repre- sentation of an object that is displayed on the display of the accessory device. The user interface object may be user- interactive, or selectable by a user input. For example, an image (e.g., icon), a button, and text (e.g., hyperlink) each optionally constitute a user interface object. The user inter- face object may form part of a widget. A widget may be seen as a mini-application that may be used by the user and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user-interface objects.

The processor of the accessory device may be configured to display, on the display, one or more user interfaces, such as user interface screens, including a first user interface and/or a second user interface. A user interface may com- prise one or more, such as a plurality of user interface objects. For example, the first user interface may comprise a first user interface object. A second user interface may comprise a second user interface object. A user interface object, such as the first user interface object and/or the second user interface object, may represent an operating state of the base plate. For example, the first user interface may comprise a first primary user interface object and/or a first secondary user interface object. A second user interface may comprise a second primary user interface object and/or a second secondary user interface object. A user interface object, such as the first primary user interface object and/or the second primary user interface object, may represent an operating state of the base plate.

An accessory device is disclosed, e.g. for or of an ostomy system comprising a monitor device and an ostomy appli- ance, the ostomy appliance comprising a base plate, the accessory device comprising a memory; a processor; and an interface coupled to the processor and configured to com- municate with the monitor device, wherein the interface comprises a display and is configured to obtain monitor data from the monitor device coupled to the ostomy appliance. The processor is configured to obtain a base plate identifier of the base plate; obtain one or more base plate parameters of the base plate based on the base plate identifier, the one or more base plate parameters including a first base plate parameter; determine an operating state of the base plate based on the first base plate parameter and/or the monitor data; and display, on the display, a first user interface comprising a first user interface object representing the operating state of the base plate.

It is an advantage of the present disclosure that a user of an ostomy appliance or a health care professional is given herein improved tools to monitor and plan the use of the ostomy appliance with daily life by exploiting accessory data obtainable by the accessory device. The present disclo- sure provides an improved accuracy in monitoring and prediction of performance of an ostomy appliance with an improved degree of comfort for a user. The present disclo- sure permits deriving operating states in a more accurate manner by a base plate identifier that is seen as affecting the operating state. In other words, the disclosed server device and accessory device allow to anticipate and indicate the dynamic internal of the base plate to a user, which supports the user in coordinating the use of the ostomy appliance/base plate with the planning of daily life activities.

An operating state of the base plate in the present disclo- sure is indicative of the dynamic internal state of the ostomy appliance, (e.g. of the base plate of the ostomy appliance currently being worn by the user) optionally related to adhesive performance of the base plate/ostomy appliance. Adhesive performance of the ostomy appliance may be related to an internal condition of the ostomy appliance (e.g. of the base plate of the ostomy appliance), such as an internal condition of an adhesive layer of the base plate. The adhesive performance, and thereby the operating state may be affected by several factors, such as humidity, temperature, misplacement of the ostomy appliance on the stoma, and/or malfunction of the ostomy appliance. The one or more factors alone or in combination impact the adhesive performance of the ostomy appliance. The operating state may be varying in time. The operating state may be indicative of a degree of erosion of the base plate.

Adhesive performance may be indicative of wear property, e.g. wear time and/or wear comfort. The operating state may comprise at least one of: a wear time, a quality of adhesion, and a moisture pattern representation. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time. A quality of adhesion may comprise a metric indicative of erosion of a layer of the base plate, such as of the first adhesive layer. A moisture pattern representation may comprise one or more metrics or parameters representative or indicative of a moisture pattern (e.g. a moisture pattern type), e.g. a moisture pattern of the first adhesive layer.

An operating state may be configured to indicate whether the ostomy appliance or the base plate thereof is properly operational based on its adhesive performance (e.g. wear property, e.g. wear time and/or wear comfort). For example, the operating state may be indicative of the severity and/or imminence of a leakage (e.g. low, medium, acute). The operating state may comprise Z operating states, where Z is an integer. The operating state may comprise a first operating state, a second operating state, and/or a third operating state (e.g. good, check, change in X time/NOW).

The processor of the accessory device is configured to obtain a base plate identifier of the base plate. A base plate identifier identifies a base plate or a group of base plates, such as a base plate batch and/or a base plate type or model. For example, a base plate identifier may be indicative of a base plate of one of a convex type, a concave type, or a planar type. A base plate identifier may comprise batch identifier and/or a model identifier. To obtain the base plate identifier of the base plate may comprise to receive and/or retrieve the base plate identifier from the monitor device e.g. as part of monitor data from the monitor device. To obtain the base plate identifier of the base plate may comprise to receive a user input on the display, the user input being indicative of the base plate identifier. To obtain the base plate identifier of the base plate may comprise to obtain image data indicative of the base plate identifier, e.g. with a camera of the accessory device, and derive the base plate identifier from the image data. The image data may comprise a bar code, such as a linear barcode or a matrix (2D) barcode.

In the accessory device, to obtain one or more base plate parameters of the base plate may comprise to transmit the base plate identifier to a server device and/or receive the one or more base plate parameters including the first base plate parameter from the server device. The first base plate parameter may be based on accessory data from a set of accessory devices.

A base plate parameter, such as first base plate parameter and/or second base plate parameter, may be indicative of a base plate property, such as electrode configuration of the base plate (optionally including but not limited to position (electrode distance) and/or number of electrodes) or material of the first adhesive layer (or parameters related thereto).

In the accessory device, to obtain one or more base plate parameters of the base plate may comprise to transmit accessory data comprising the monitor data to the server device, and wherein the one or more base plate parameters of the base plate is based on the monitor data.

In the accessory device, to determine an operating state of the base plate based on the first base plate parameter and/or the monitor data may comprise to determine an estimate of remaining wear time of the base plate, and wherein the first user interface object represents the estimate of remaining wear time of the base plate.

The monitor data may comprise ostomy data obtained from electrodes of the base plate. Thus, to obtain monitor data may comprise to obtain ostomy data from the monitor device.

The monitor data may comprise parameter data based on ostomy data from electrodes of the base plate. Thus, to obtain monitor data may comprise to obtain parameter data (first parameter data, second parameter data and/or third parameter data) from the monitor device. Thus, the monitor data may comprise parameter data (first parameter data, second parameter data and/or third parameter data). The monitor data may comprise sensor data of one or more sensors of the monitor device. Thus, to obtain monitor data may comprise to obtain sensor data from the monitor device.

The first parameter data, the second parameter data, and the third parameter data may be indicative of resistance between the first electrode pair, the second electrode pair, and the third electrode pair, respectively. The first parameter data, the second parameter data, and the third parameter data may be indicative of voltage between the first electrode pair, the second electrode pair, and the third electrode pair, respectively (and thus indicative of resistance). The first parameter data, the second parameter data, and the third parameter data may be indicative of current between the first electrode pair, the second electrode pair, and the third electrode pair, respectively (and thus indicative of resistance).

The first parameter data, the second parameter data, and the third parameter data may be indicative of a rate of change in resistance between the first electrode pair, the second electrode pair, and the third electrode pair, respectively. In one or more exemplary monitor devices, the first parameter data, the second parameter data, and the third parameter data may be indicative of a rate of change in voltage between the first electrode pair, the second electrode pair, and the third electrode pair, respectively. In one or more exemplary monitor devices, the first parameter data, the second parameter data, and the third parameter data may be indicative of a rate of change in current between the first electrode pair, the second electrode pair, and the third electrode pair, respectively.

The processor of the accessory device is configured to determine an operating state of the base plate based on the first base plate parameter and/or the monitor data, such as one or more of ostomy data, parameter data, and sensor data. The processor of the accessory device may be configured to determine an operating state of the base plate based on the first base plate parameter and accessory data including the monitor data, such as one or more of ostomy data, parameter data, and sensor data.

In one or more exemplary accessory, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary accessory devices, to determine an operating state of the base plate may be based on a first threshold set comprising one or a plurality of first threshold values. The first threshold set may comprise one or a plurality of threshold values, e.g. to be applied in the first criteria set. The first threshold set may be selected based on the base plate identifier and/or the first base plate parameter. The first threshold set may comprise a first primary threshold value. The first threshold set may comprise a first secondary threshold value. The first threshold set may comprise a first tertiary threshold value.

The first criteria set may be given by or at least may comprise:

$(P\_1\_1 < TH\_1\_1)$,
$(P\_2\_1 > TH\_1\_2)$, and
$(P\_3\_1 > TH\_1\_3)$, wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate. The first threshold values ($TH\_1\_1$, $TH\_1\_2$ and $TH\_1\_3$) may be the same or different, e.g. depending on the electrode configuration of the base plate. The first tertiary criterion ($P\_3\_1 < TH\_1\_3$) may be omitted in the first criteria set. The first operating state, e.g. indicative of low degree of radial erosion on the base plate may be indicative of a radial progression of moisture to the first electrode pair (but not to the second electrode pair and not to the third electrode pair) which corresponds to e.g. an un-alarming and/or normal radial progression of moisture.

The first criteria set may be different for different base plate identifiers/first base plate parameters. The first threshold values ($TH\_1\_1$, $TH\_1\_2$ and $TH\_1\_3$) may be different for different base plate identifiers. The first threshold values ($TH\_1\_1$, $TH\_1\_2$ and $TH\_1\_3$) may form respective base plate parameters of the base plate. The first base plate parameter may be indicative of the first threshold values.

In one or more exemplary accessory devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary accessory devices, to determine an operating state of the base plate is based on a second threshold set comprising one or a plurality of second threshold values. The second threshold set may comprise one or a plurality of threshold values, e.g. to be applied in the second criteria set. The second threshold set may be selected based on the base plate identifier and/or the first base plate parameter. The second threshold set may comprise a second primary threshold value. The second threshold set may comprise a second secondary threshold value. The second threshold set may comprise a second tertiary threshold value.

The second criteria set may be given by or at least may comprise:

$(P\_1\_1 < TH\_2\_1)$,
$(P\_2\_1 < TH\_2\_2)$, and
$(P\_3\_1 > TH\_2\_3)$ wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate. The second threshold values ($TH\_2\_1$, $TH\_2\_2$ and $TH\_2\_3$) may be the same or different, e.g. depending on the electrode configuration of the base plate. The second primary criterion ($P\_1\_1 < TH\_2\_1$) and/or the second tertiary criterion ($P\_3\_1 > TH\_2\_3$) may be omitted in the second criteria set. The second operating state indicative of medium degree of radial erosion on the base plate may be indicative of a radial progression of moisture to the first electrode pair and the second electrode pair (and not the third electrode pair). The second operating state indicative of medium degree of radial erosion on the base plate may be indicative of a radial progression of moisture to the first electrode pair and to the second electrode pair.

The second criteria set may be different for different base plate identifiers/first base plate parameters. The second threshold values ($TH\_2\_1$, $TH\_2\_2$ and $TH\_2\_3$) may be different for different base plate identifiers. The second threshold values ($TH\_2\_1$, $TH\_2\_2$ and $TH\_2\_3$) may form respective base plate parameters of the base plate. The first base plate parameter may be indicative of the second threshold values.

In other words, the first base plate parameter may function as a criteria selector indicative of which criteria to apply in determining the operating state of the base plate.

The processor of the accessory device may be configured to display, on the display, a first user interface comprising a first user interface object representing the operating state of the base plate, e.g. in accordance with a display criterion being satisfied.

In the accessory device, to determine an operating state of the base plate may comprise to determine an estimate of remaining wear time of the base plate, e.g. based on the first base plate parameter and/or accessory data, such as sensor data of the monitor device and/or one or more of ostomy data and parameter data based on ostomy data. The first base plate parameter may be indicative of the remaining wear time and/or indicative of one or more velocities to apply in determining the remaining wear time. In other words, the first base plate parameter may function as a velocity selector indicative of which velocities to apply in determining an estimate of remaining wear time of the base plate (e.g. as part of the operating state of the base plate. The first user interface object may represent the estimate of remaining wear time of the base plate. In one or more exemplary accessory devices, the display criterion may be satisfied if the estimate of the remaining wear time of the base plate is less than a display threshold.

In the accessory device, to determine an estimate of remaining wear time of the base plate may comprise to determine a change in a current estimate of remaining wear time of the base plate. The estimate of estimate of remaining wear time of the base plate may be based on the current estimate of remaining wear time and the change in the current estimate of remaining wear time.

In the accessory device, to determine an estimate of remaining wear time of the base plate may comprise to increase a current estimate of remaining wear time of the base plate in accordance with a set of increase criteria being satisfied. The set of increase criteria may comprise one or more increase criteria.

In the accessory device, to determine an estimate of remaining wear time of the base plate may comprise to reduce a current estimate of remaining wear time of the base plate in accordance with a set of reduction criteria being satisfied. The set of reduction criteria may comprise one or more reduction criteria.

The accessory data may comprise user data of a user of the ostomy appliance. Thus, to obtain accessory data may comprise to obtain user data, e.g. from the memory of the accessory device and/or via the interface of the accessory device.

The first user interface object may be a notification, e.g. wherein the first user interface is a lock screen or a home screen of the accessory device.

The first user interface object may be an application launch icon and the first user interface may be a home screen.

The first user interface may be an application user interface of an application running on the accessory device.

A server device for or of an ostomy system of a user is disclosed, the ostomy system comprising a monitor device, an ostomy appliance, and an accessory device, the ostomy appliance comprising a base plate.

The server device comprises a memory; one of more processors; and an interface coupled to the one or more processors and configured to communicate with the accessory device, e.g. via a network.

The one or more processors are configured to obtain accessory data and associated base plate identifiers from a set of accessory devices; obtain a base plate identifier of a base plate from the accessory device; and determine a first base plate parameter of the base plate based on the base plate identifier.

In one or more exemplary server devices, the one or more processors are configured to transmit the first base plate parameter to the accessory device.

In one or more exemplary server devices, the one or more processors are configured to determine an operating state of the base plate based on the first base plate parameter and/or the accessory data including monitor data; and transmit an operating state identifier indicative of the operating state to the accessory device.

The first base plate parameter may be based on the accessory data from the set of accessory devices. The accessory data from the set of accessory devices may comprise monitor data from monitor devices. Thus, the first base plate parameter may be based on monitor data from the set of accessory devices. The monitor data from the set of accessory devices may comprise ostomy data obtained from electrodes of base plates with the associated base plate identifiers. Thus, the first base plate parameter may be based on ostomy data from the set of accessory devices. The monitor data from the set of accessory devices may comprise parameter data based on ostomy data from electrodes of base plates with the associated base plate identifiers.

It is an advantage of the present disclosure that a new user of an ostomy appliance can benefit from other user's experiences with an ostomy appliance thereby reducing the "training period" for the ostomy system of a new user. Accordingly, an accurate determination of operating state of the base plate for new or relatively new users is provided.

The one or more processors of the server device are configured to determine a first base plate parameter of the base plate based on the base plate identifier. The first base plate parameter may be a wear property of the base plate associated with the base plate identifier, e.g. wear time and/or wear comfort. The first base plate parameter may comprise at least one of: a wear time, a quality of adhesion, and a moisture pattern representation of the base plate. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time. The first base plate parameter may be wear time, such as a baseline wear time, of the base plate associated with the base plate identifier.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The base plate 4 and the monitor device 6 are in a coupled state, and the monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. The monitor data may include sensor data of the monitor device. In the illustrated ostomy system, the accessory device 8 is a mobile phone or smartphone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a center point 19. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
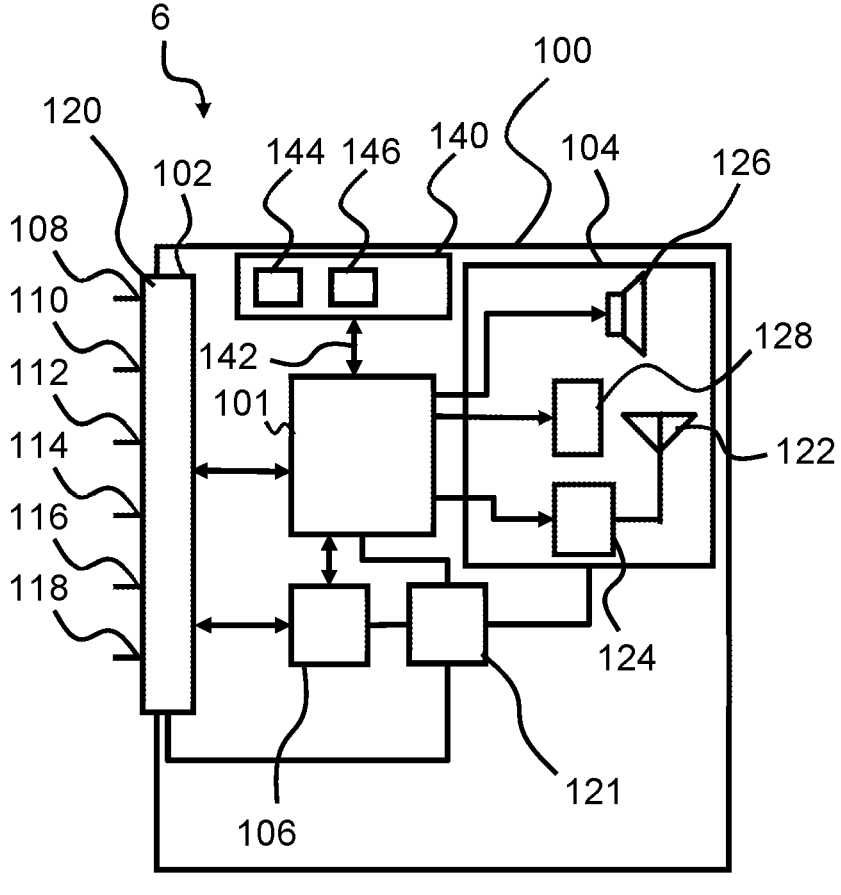
FIG. 2 illustrates an exemplary monitor device of the ostomy system.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101 for provision of sensor data 142 to the processor 101. The sensor unit 140 comprises a first sensor 144 being a temperature and humidity sensor for feeding temperature and humidity data as sensor data 142 to the processor 101. Further, the sensor unit 140 comprises a second sensor 146 being an accelerometer for feeding acceleration data as sensor data 142 to the processor 101. The processor 101 receives and stores sensor data 142 comprising temperature data, humidity data, and acceleration data, in the memory 106 and/or transmits the sensor data as part of monitor data via second interface 104.

The monitor device 100 is configured to obtain ostomy data from the base plate coupled to the first interface 102. The ostomy data may be stored in the memory 106 and/or processed in the processor 101 in order to obtain parameter data based on the ostomy data.

Figure 3:
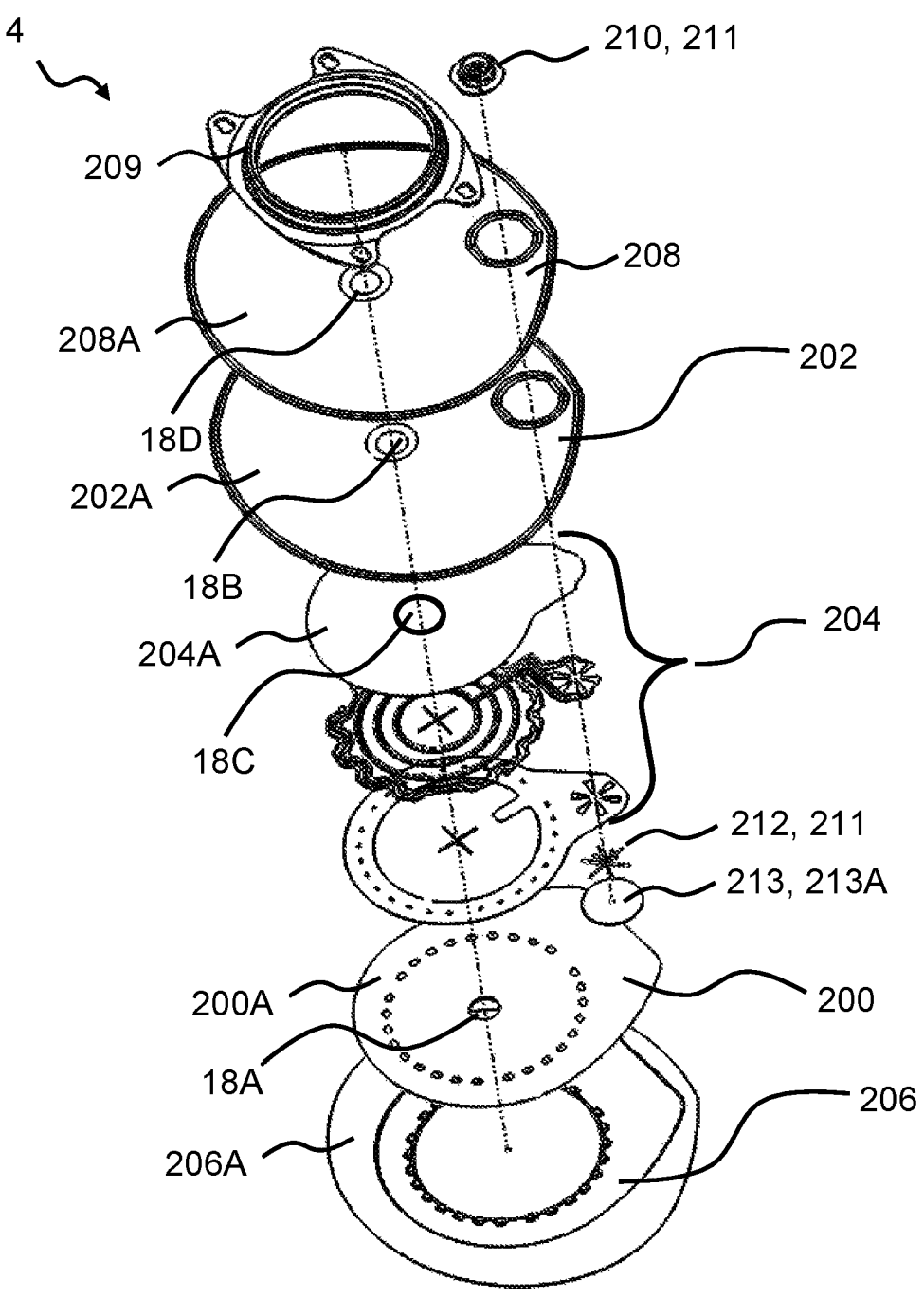
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202 with a stomal opening 18B. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
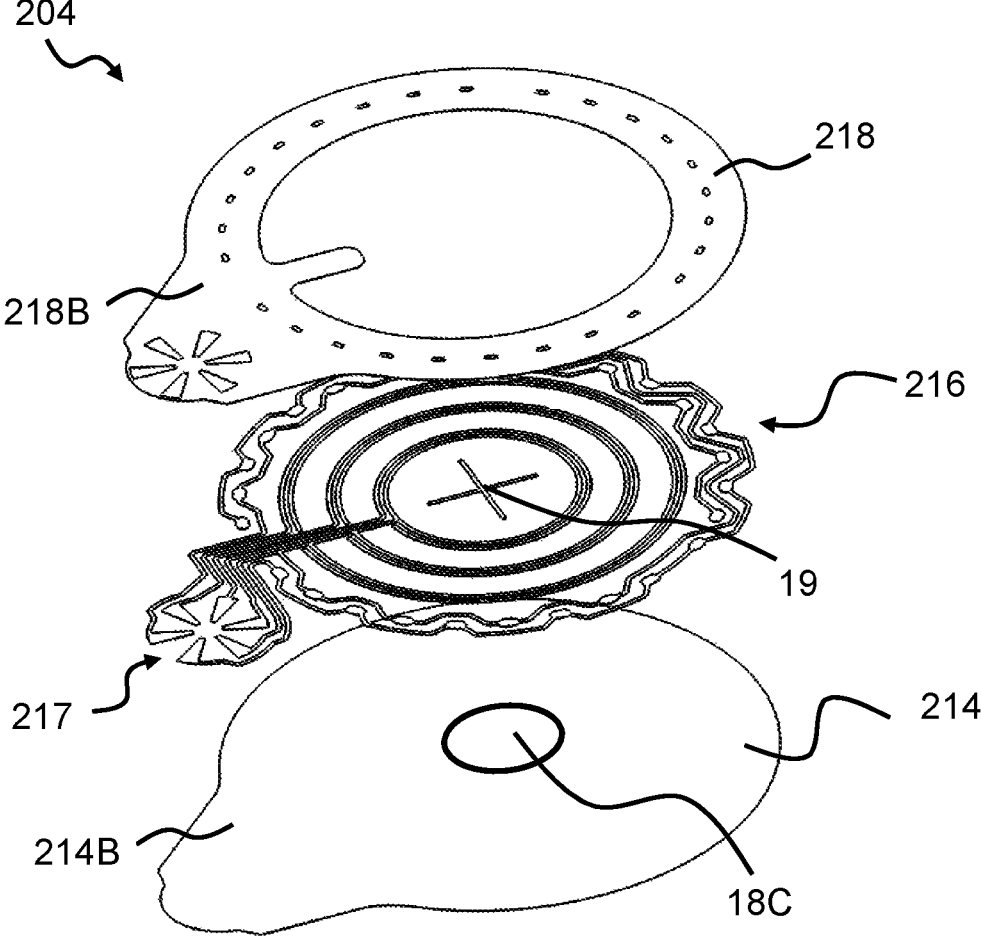
FIG. 4 is an exploded view of an exemplary electrode assembly.

FIG. 4 illustrates an exploded view of an exemplary electrode assembly 204 of a base plate. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
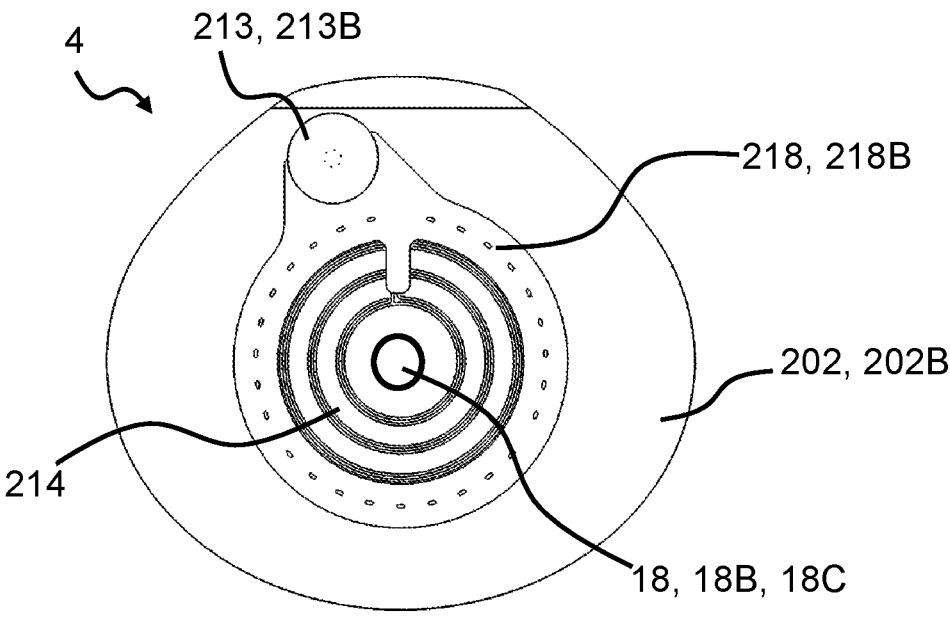
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
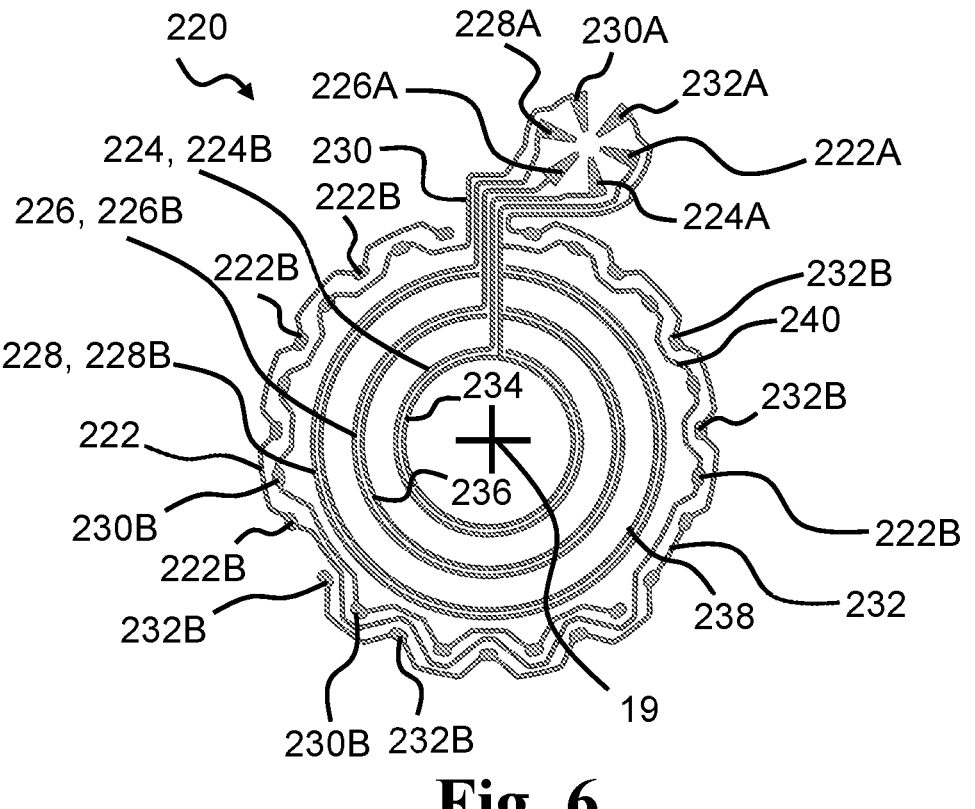
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

The first sensing part 224B extends circularly at least 330 degrees around the stomal opening at a first radial distance R1 from the center point 19. The first radial distance R1 may be around 14 mm. In one or more embodiments, the first radial distance R1 may be around 13 mm, such as 12.5 mm. The first electrode part 234 is arranged on the inside of the first sensing part (i.e. closer to the center point) and extends circularly at least 330 degrees around the stomal opening at a first ground distance RG1 from the first sensing part (radially from the center point). The first ground distance RG1 between sensing part of first electrode and first electrode part is about 1 mm.

The second sensing part 226B extends circularly at least 330 degrees around the stomal opening at a second radial distance R2 from the center point 19. The second radial distance R2 may be 18 mm. In one or more embodiments, the second radial distance R2 may be 17 mm. The second electrode part 236 is arranged on the inside of the second sensing part 226B (i.e. closer to the center point) and extends circularly at least 330 degrees around the stomal opening at a second ground distance RG2 from the second sensing part 226B (radially from the center point). The second ground distance RG2 between sensing part of second electrode and second electrode part is about 1 mm.

The third sensing part 228B extends circularly at least 330 degrees around the stomal opening at a third radial distance R3 from the center point 19. The third radial distance R3 is about 26 mm. In one or more embodiments, the third radial distance R3 is 21 mm. The third electrode part 238 is arranged on the inside of the third sensing part 228B (i.e. closer to the center point) and extends circularly at least 330 degrees around the stomal opening at a third ground distance RG3 from the third sensing part 228B (radially from the center point). The third ground distance RG3 between sensing part of third electrode and third electrode part is about 1 mm.

The ground electrode 222 comprises a fourth electrode part 240 for forming a ground or reference for the fourth electrode 230 and the fifth electrode 232. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the center point 19 at a leakage radius from the center point (such as a leakage radius R5 which may be around 32 mm from the center point). The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm.

Figure 7:
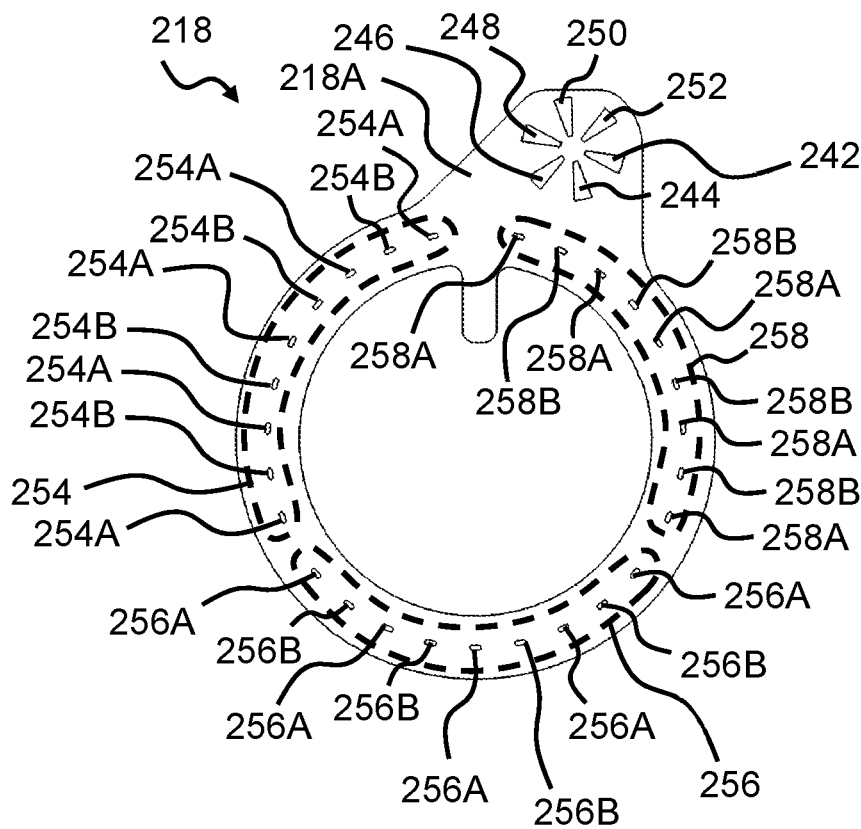
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
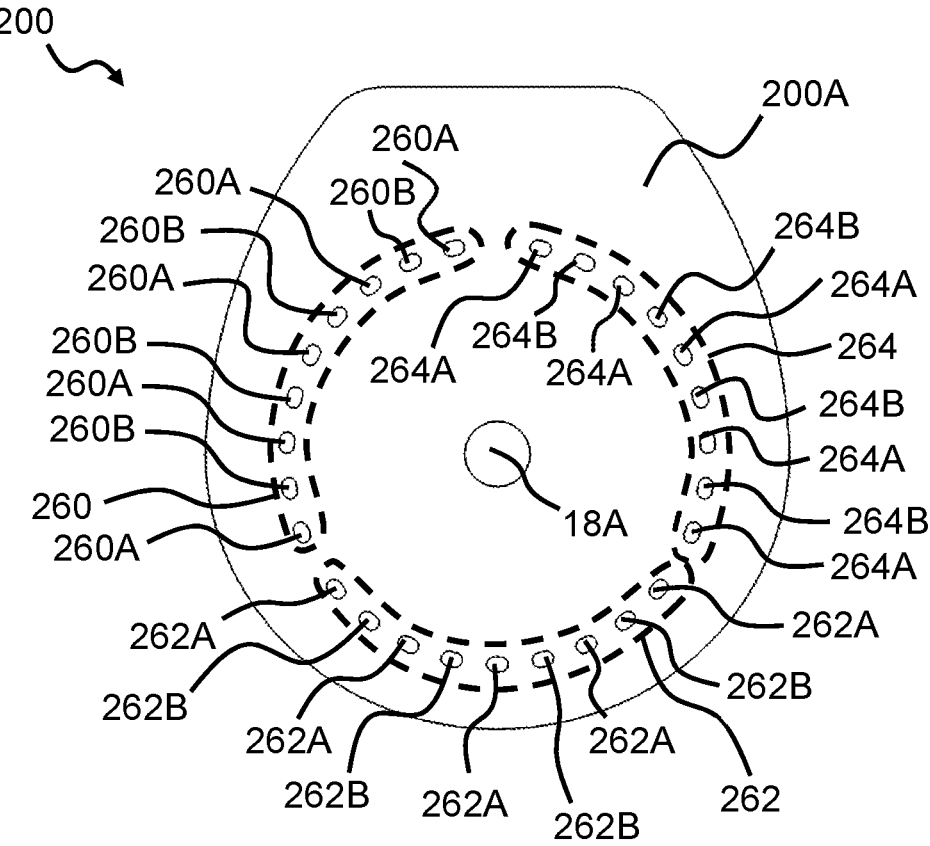
FIG. 8 is a distal view of an exemplary first adhesive layer.
Figure 9:
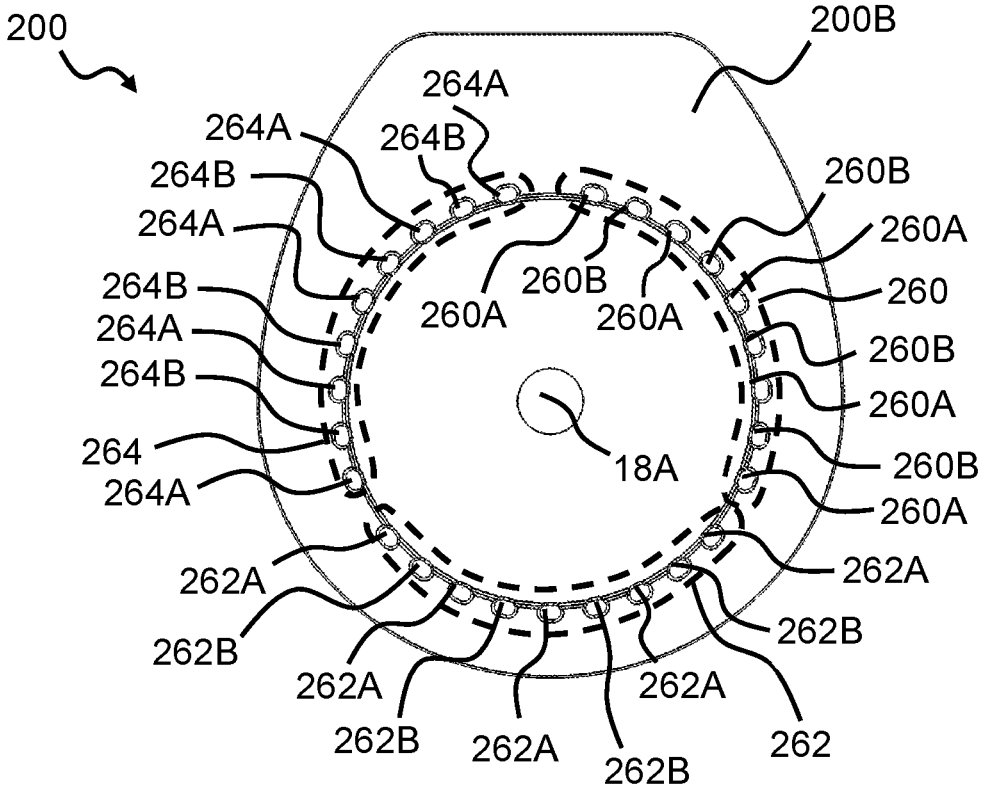
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings comprise, in the illustrated exemplary first adhesive layer, five primary first sensor point openings 260A each configured to overlap a part of the ground electrode 222. The primary sensor point openings comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings comprise, in the illustrated exemplary first adhesive layer, five secondary first sensor point openings 262A each configured to overlap a part of the fifth electrode 232. The secondary sensor point openings comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings comprise, in the illustrated exemplary first adhesive layer, five tertiary first sensor point openings 264A each configured to overlap a part of the fifth electrode 232. The tertiary sensor point openings comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
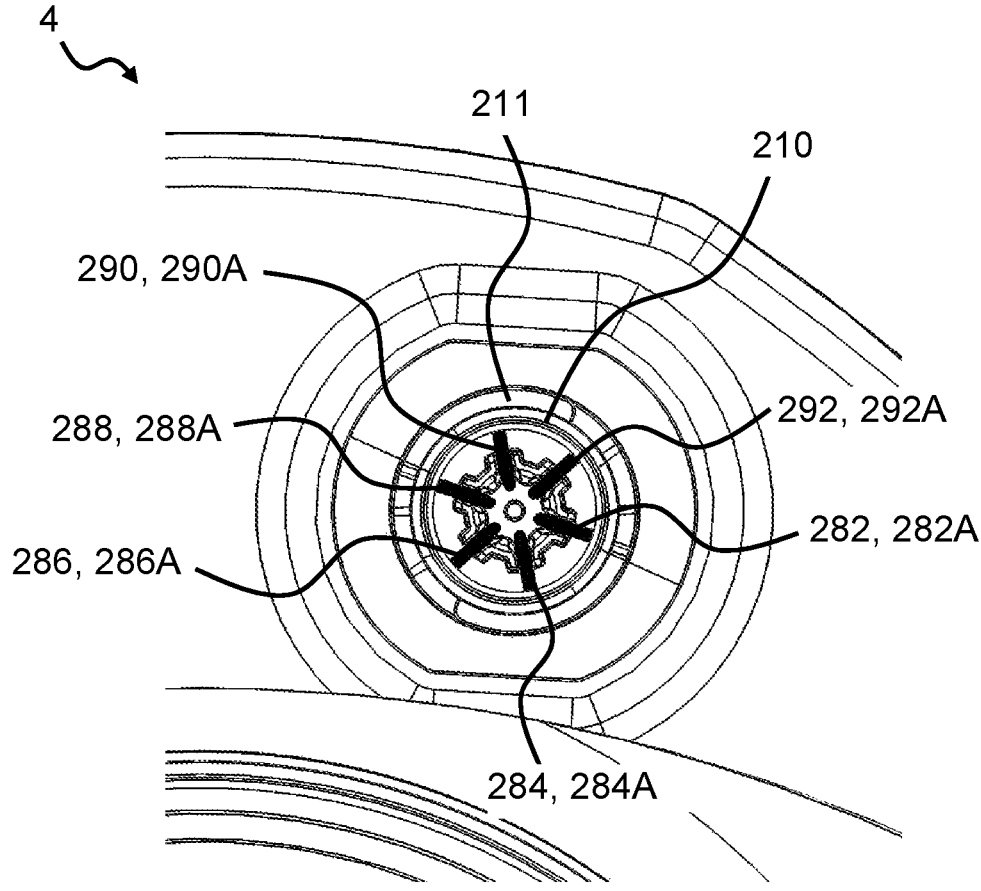
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 211/monitor interface comprises a plurality of terminals formed by respective terminal elements for forming respective electrical connections with respective terminals of the monitor device.

The plurality of terminals of the first connector 211/monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of base plate.

Figure 11:
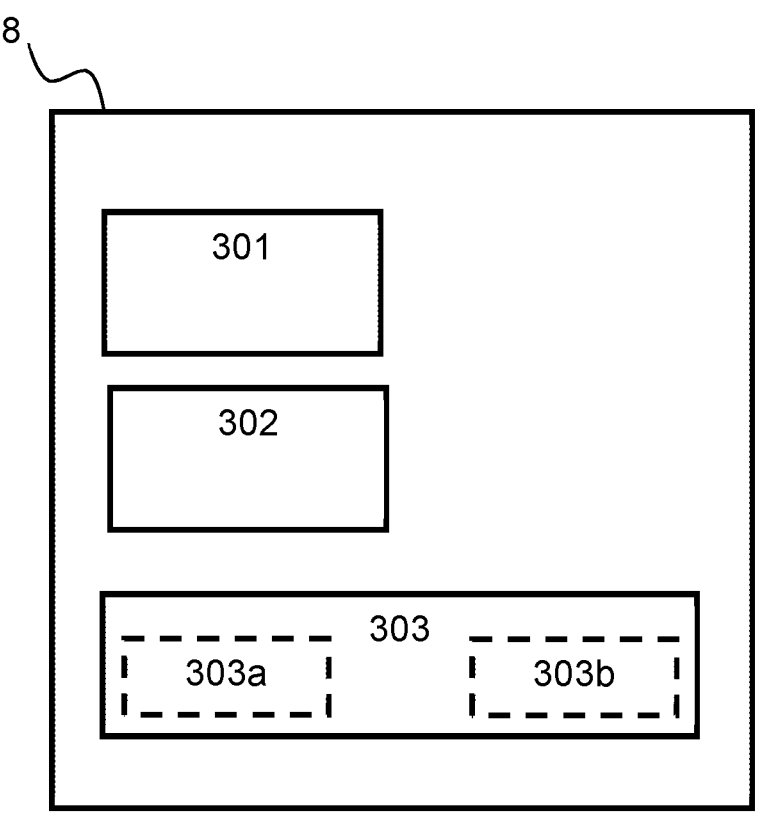
FIG. 11 illustrates an exemplary accessory device according to the present disclosure.

FIG. 11 is a block diagram illustrating an exemplary accessory device 8 according to the present disclosure. The accessory device 8 is a mobile phone or smartphone and forms part of an ostomy system 1 and is capable of determining operating states of an ostomy appliance 2 to be placed on a user's skin, in particular determining an operating state of the base plate 4 of the ostomy appliance based on the accessory data and/or first base plate parameter from server device. The accessory device 8 comprises a memory 301; a processor 302 coupled to the memory 301; and an interface 303 coupled to the processor 302.

The interface 303 comprises a display 303a and a transceiver unit 303b comprising a transceiver and an antenna. The interface 303 is configured to obtain monitor data from the monitor device coupled to the ostomy appliance, such as to receive or retrieve the monitor data from the monitor device via the transceiver unit 303b. The monitor data or at least parts thereof may be stored in the memory 301.

Figure 12:
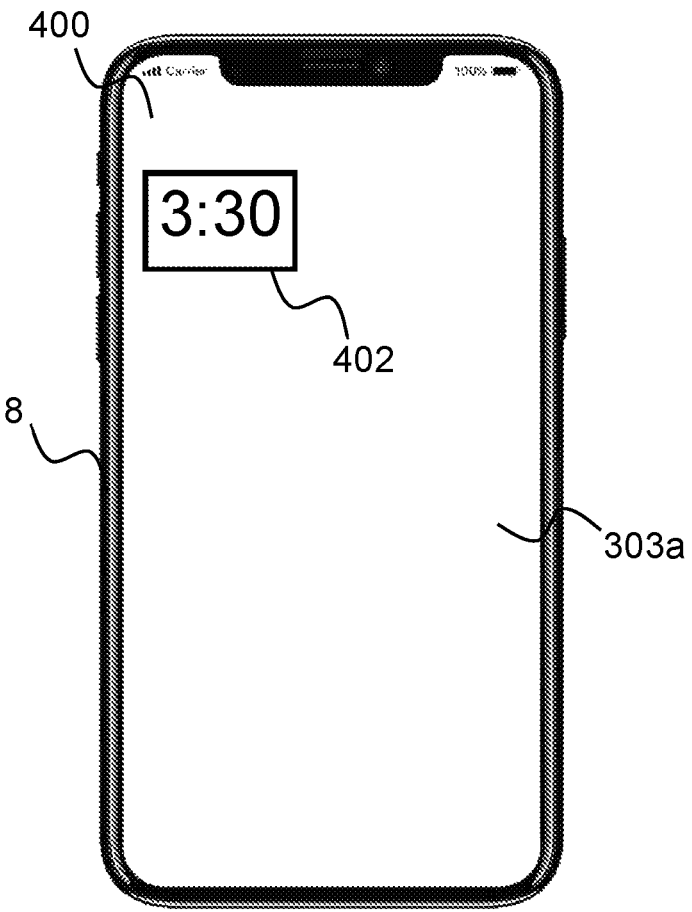
FIG. 12 illustrates an exemplary accessory device according to the present disclosure.

The processor 302 is configured to obtain a base plate identifier of the base plate; obtain one or more base plate parameters of the base plate based on the base plate identifier, the one or more base plate parameters including a first base plate parameter; determine an operating state of the base plate based on the first base plate parameter and the monitor data; and display, on the display 303a, a first user interface 400 comprising a first user interface object 402 representing the operating state of the base plate, see FIG. 12.

The processor 302 is configured to communicate with one or more devices of the ostomy system. The one or more devices comprise a monitor device disclosed herein, and a server device disclosed herein.

The interface 303 is configured to obtain monitor data from the one or more devices via transceiver unit 303b. The monitor data may be indicative of a condition of the ostomy appliance, such as a condition of a proximal side of a layer of the ostomy appliance (e.g. a first adhesive layer of the base plate) that is directed towards the skin surface.

In the accessory device 8, to obtain one or more base plate parameters of the base plate comprises to transmit the base plate identifier to server device 10 via the transceiver unit 303b and receive the one or more base plate parameters including the first base plate parameter from the server device via the transceiver unit 303b.

Optionally, to obtain one or more base plate parameters of the base plate comprises to transmit accessory data comprising the monitor data to the server device via the transceiver unit 303b, and wherein the one or more base plate parameters of the base plate is based on the monitor data.

The processor 302 is configured to determine an operating state of the base plate based on the first base plate parameter and/or the monitor data; and display, on the display 303a, a first user interface comprising a first user interface object representing the operating state of the base plate. The accessory device 8 may be configured to communicate the operating state, via the display 303a or the transceiver unit 303b, e.g. to the user, and/or to other devices.

In the accessory device 8, to determine an operating state of the base plate optionally comprises to determine an estimate of remaining wear time of the base plate based on the first base plate parameter and optionally the monitor data e.g. one or more of ostomy data, parameter data and sensor data, and wherein the first user interface object represents the estimate of remaining wear time of the base plate. To determine an estimate of remaining wear time of the base plate optionally comprises to determine a change in a current estimate of remaining wear time of the base plate, wherein the estimate of remaining wear time of the base plate is based on the current estimate of remaining wear time and the change in the current estimate of remaining wear time. The first base plate parameter is based on accessory data, e.g. monitor data, from a set of accessory devices.

The processor 302 may be configured to determine the operating state of the base plate by determining a current moisture pattern type based on the first base plate parameter and/or accessory data, and by generating the operating state based on the current moisture pattern types and the sensor data of the monitor device. Determining a current moisture pattern type may be based on the first base plate parameter and/or accessory data.

The processor 302 may be configured to determine the operating state based on a current operating state, and optionally any prior operating state prior to the determining of the operating state.

To determine an operating state of the base plate of the ostomy appliance may comprise to determine an operating state from a set of operating states. In other words, to determine an operating state may comprise selecting an operating state from a set of predefined operating states based on the first base plate parameter and/or accessory data. The set of predefined operating states may comprise a number of operating states, such as at least two operating states, at least three operating states, at least four operating states, or at least five operating states. The number of operating states may be in the range from four to twenty. In one or more exemplary accessory devices, the number of operating states in the set of predefined operating states is larger than ten, such as larger than 20 or even larger than 50.

The processor 302 may be configured to display, on the display, a first user interface comprising a first user interface object representing the operating state of the base plate by notifying the user via the interface 303, such as by displaying a notification on display 303*a* of the accessory device 8. The notification may comprise the first user interface object representative of the operating state. The notification may comprise a notification indicator to open an application related to the ostomy appliance.

FIG. 12 shows an exemplary accessory device 8 displaying a first user interface 400 on display 303*a*. The first user interface 400 comprises first user interface object 402 representing an estimate of remaining wear time (3 hours and 30 minutes) determined by the processor of the accessory device 8.

Figure 13:
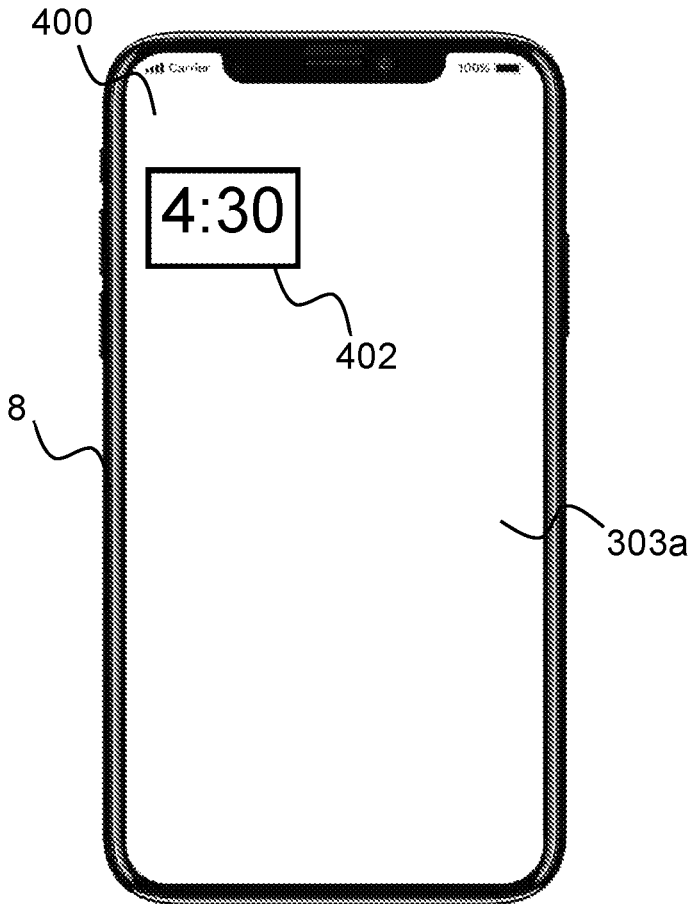
FIG. 13 illustrates an exemplary accessory device according to the present disclosure.

FIG. 13 shows an exemplary accessory device 8. The processor of accessory device 8 has determined a change of 1 hour in a current estimate of remaining wear time of 3 hours and 30 minutes and has determined an estimate of remaining wear time as a sum of the current estimate and the change to obtain an estimate of remaining wear time of 4 hours and 30 minutes, which is represented by the first user interface object 402 of the first user interface 400.

Figure 14:
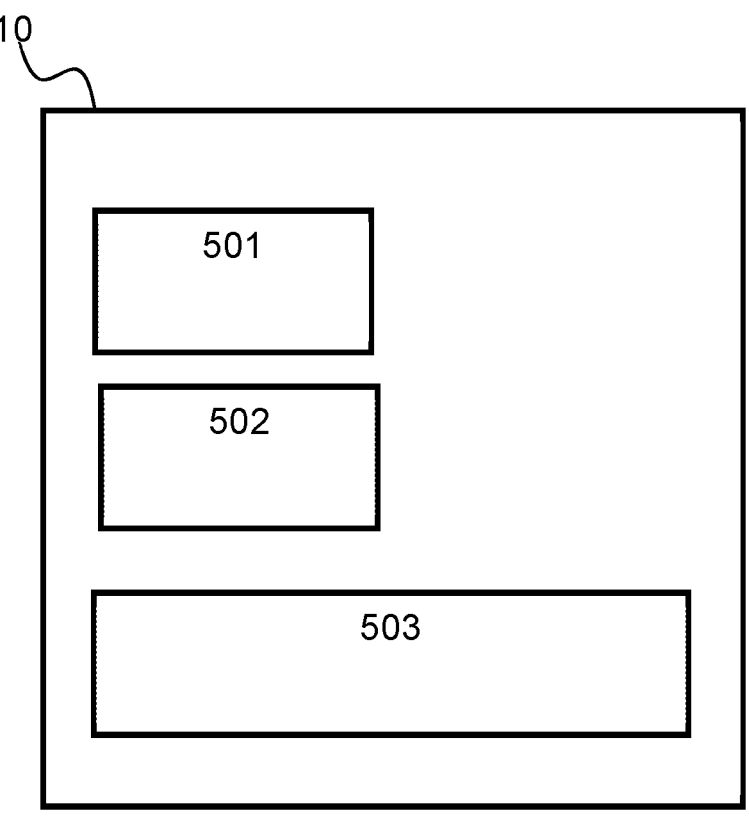
FIG. 14 illustrates an exemplary server device according to the present disclosure.

FIG. 14 is a block diagram illustrating an exemplary server device 10 according to the present disclosure. The server device 10 forms part of an ostomy system 1 comprising a monitor device, an ostomy appliance, and an accessory device, the ostomy appliance comprising a base plate, the server device 10 optionally being capable of selecting a user type of a user and determining base plate parameter(s) based on the user type. The server device 10 comprises a memory 501; one or more processor 502 coupled to the memory 501; and an interface 503 coupled to the one or more processors 502 and configured to communicate with the accessory device.

The one or more processors 502 are configured to obtain accessory data and associated base plate identifiers from a set of accessory devices by receiving and/or retrieving the accessory data and associated base plate identifiers via the interface 503. By obtaining accessory data with associated base plate identifiers from a large number of accessory devices, accessory data including monitor data for a large number of users can be grouped and handled based on the respective base plate (with associated respective base plate identifier) that was worn when the accessory data where obtained. Thereby, operating state determination/wear time estimation can be adjusted based on accessory data for different base plate batches (base plate identifiers enable grouping into respective base plate batches). For example, a first base plate may belong to a first batch of base plates which has a larger or smaller wear time than base plates of a second batch of base plates, e.g. due to variations in manufacturing. Further, operating state determination/wear time estimation can be adjusted based on accessory data for different base plate models or types. For example, a first base plate may be of a first type which has a larger wear time than base plates of a second type.

Further, the one or more processors 502 are configured to obtain a base plate identifier of a base plate from the accessory device; and determine a first base plate parameter of the base plate based on the base plate identifier and the accessory data from the set of accessory devices. The first base plate parameter may be wear time, such as a baseline wear time, associated or corresponding to the base plate identifier. The one or more processors 502 are configured to transmit the first base plate parameter to accessory device via the interface 503.

In the server device 10, the accessory data from the set of accessory devices comprises monitor data from monitor devices transmitted to the set of accessory devices. Thus, the one or more processors 502 are configured to determine a first base plate parameter of the base plate based on monitor data, e.g. comprising one or more of ostomy data, parameter data, and sensor data, from the set of accessory devices.

Figure 15A:
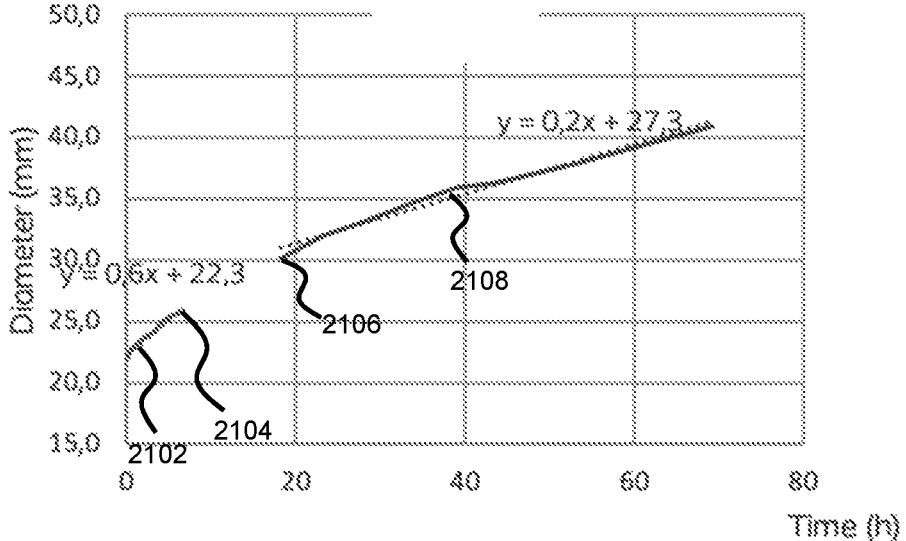
FIGS. 15A and 15B are exemplary graphical representations of moisture propagation in different base plate types.
Figure 15B:
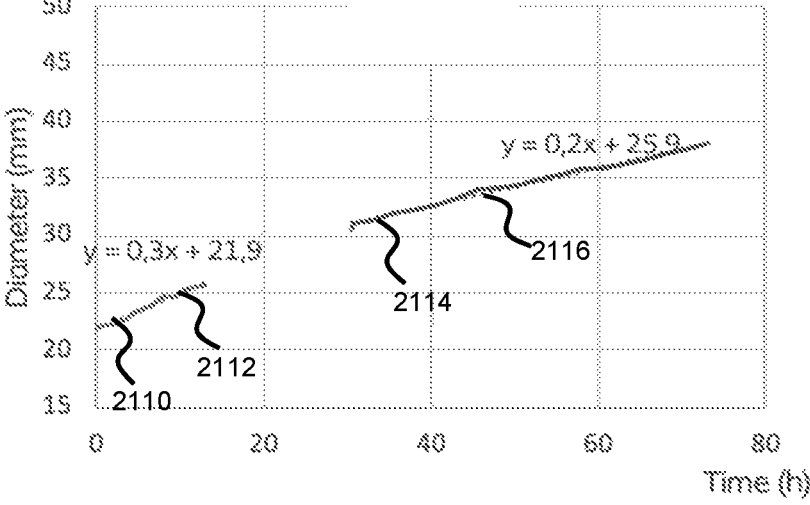

FIGS. 15A-15B show exemplary graphical representations of a whitening zone diameter (e.g. related to a radial thickness of a whitening ring surrounding the stomal opening) as a function of time for base plates of different types (different adhesive layer material). FIGS. 15A-15B illustrate the moisture propagation in the first adhesive layer as a function of time, and illustrate a diametral velocity of the moisture propagation on the proximal surface of the first adhesive layer of the base plate. The actual moisture propagation in the first adhesive layer may appear as a whitening zone (e.g. a white ring around the stomal opening) in the first adhesive layer. FIGS. 15A-15B show measurements of a diameter of the whitening zone as a function of time as moisture propagates. Moisture affects the first adhesive layer in that the moisture reacts with the composition of the first adhesive layer to form the white ring around the stomal opening, and thereby reduces adhesive performance of the base plate.

FIG. 15A is obtained by experiments where water is applied from the stomal opening of the base plate of a first type to measure a velocity of the radial propagation of moisture leading to radial erosion of the first adhesive layer of the base plate of the first type.

FIG. 15B is obtained by experiments where water is applied from the stomal opening of the base plate of a second type to measure a velocity the radial propagation of moisture leading to radial erosion of the first adhesive layer of the base plate of the second type. The second type is different from the first type, in that the composition of the first adhesive layer in the first type is different from the first adhesive layer of the second type when compared to the first type.

Curve 2104 shows, as a function of time, a diameter of the white ring of a base plate of the first type measured from a cut for a stomal opening to the first electrode pair.

Curve 2102 shows a linear approximation of curve 2104, and thereby characterizes the velocity from the cut to the first electrode pair. The linear approximation may be formulated as a linear equation of the type $Y=v01*X+A$, where Y is the diameter of the white ring in millimetres (mm), X is time in hours, v01 is a diametral velocity of propagation of moisture in the base plate of the first type from the cut to the first electrode pair, and A relates to the diameter of the cut. In the experiment illustrated in FIG. 15A, v01=0.6 mm/h and A is 22 (i.e. the cut for the stomal opening has a diameter of 22 mm). Other experiments have shown that v01 may be in the range of 0.5 mm/h to 0.7 mm/h, with an average diametral velocity v01 of 0.65 mm/h for moisture to propagate from the cut to the first electrode pair. To obtain radial velocity V01 for moisture to propagate from the cut to the first electrode pair from the results of FIG. 15A, the diametral velocity v01 is to be divided by two: V01=0.3 mm/h for the illustrated experiment. In one or more embodiments, the radial velocity may range from 0.25 to 0.35 mm/h.

Curve 2106 shows, as a function of time, a diameter of the white ring of a base plate of the first type measured from the first electrode pair to the second electrode pair.

Curve 2108 shows a linear approximation of curve 2106, and thereby characterizes the velocity from the first electrode pair to the second electrode pair. The linear approximation may be formulated as a linear equation of the type $Y=v12*X+B$, where Y is the diameter of the white ring in millimetres (mm), X is time in hours, v12 is a diametral velocity of propagation of moisture in the base plate of the first type from the first electrode pair to the second electrode pair, and B relates to approximate location of the first electrode pair from the center of the stomal opening. In the experiment illustrated in FIG. 15A, v12=0.2 mm/h and B is 27.3 mm (i.e. the first electrode pair is placed around 27.3 mm). Other experiments have shown that v12 may be in the range of 0.15 mm/h to 0.22 mm/h, with an average diametral velocity of 0.18 mm/h for moisture to propagate from the first electrode pair to the second electrode pair. To obtain radial velocity V12 for moisture to propagate from the first electrode pair to the second electrode pair from the results of FIG. 15A, the diametral velocity v12 is to be divided by two: V12=0.1 mm/h for the illustrated experiment.

Curve 2112 shows, as a function of time, a diameter of the white ring of a base plate of the second type measured from a cut for a stomal opening to the first electrode pair.

Curve 2110 shows a linear approximation of curve 2112, and thereby characterizes the velocity from the cut to the first electrode pair. The linear approximation may be formulated as a linear equation of the type $Y=v01*X+A$, where Y is the diameter of the white ring in millimetres (mm), X is time in hours, v01 is a diametral velocity of propagation of moisture in the base plate of the second type from the cut to the first electrode pair, and A relates to the diameter of the cut. In the experiment illustrated in FIG. 15B, v01=0.3 mm/h and A is 21.9 (i.e. the cut for the stomal opening has a diameter of 21.9 mm). Other experiments have shown that v01 may be in the range of 0.2 mm/h to 0.32 mm/h, with an average diametral velocity v01 of 0.275 mm/h for moisture to propagate from the cut to the first electrode pair. To obtain radial velocity V01 for moisture to propagate from the cut to the first electrode pair from the results of FIG. 15B, the diametral velocity v01 is to be divided by two: V01=0.15 mm/h for the illustrated experiment. In one or more embodiments, the radial velocity (for a second type) may range from 0.1 to 0.15 mm/h.

Curve 2114 shows, as a function of time, a diameter of the white ring of a base plate of the second type measured from the first electrode pair to the second electrode pair.

Curve 2116 shows a linear approximation of curve 2114, and thereby characterizes the velocity from the first electrode pair to the second electrode pair. The linear approximation may be formulated as a linear equation of the type $Y=v12*X+B$, where Y is the diameter of the white ring in millimetres (mm), X is time in hours, v12 is a diametral velocity of propagation of moisture in the base plate of the second type from the first electrode pair to the second electrode pair, and B relates to approximate location of the first electrode pair from the center of the stomal opening. In the experiment illustrated in FIG. 15B, v12=0.2 mm/h and B is 25.9 mm (i.e. the first electrode pair is place around 25.9 mm). Other experiments have shown that v12 may be in the range of 0.15 mm/h to 0.22 mm/h, with an average diametral velocity of 0.1 mm/h for moisture to propagate from the first electrode pair to the second electrode pair. To obtain radial velocity V12 for moisture to propagate from the first electrode pair to the second electrode pair from the results of FIG. 15B, the diametral velocity v12 is to be divided by two: V12=0.2 mm/h for the illustrated experiment. In one or more embodiments, the radial velocity (for a second type) may range from 0.075 to 0.1 mm/h.

The radial velocities V01 and/or V12 (based on the base plate identifier) may form at least some of the one or more base plate parameters for the accessory device. In one or more exemplary embodiments, the one or more base plate parameters may be based on the radial velocities V01 and/or V12, e.g. dependent on the base plate identifier.

The experiments illustrated in FIGS. 15A-15B show that different adhesive materials of different base plate types/models (with different base plate identifiers) have different properties affecting the operating state of the respective base plate and in particular the dynamic changes in the operating state of the base plate. The present disclosure exploits knowledge on the behaviour of different base plates to determine an operating state based on monitor data and base plate identifier of the base plate.

The use of the terms "first", "second", "third" and "fourth", "primary", "secondary", "tertiary" etc. does not imply any particular order but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stomal opening
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
142 sensor data
144 first sensor
146 second sensor
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector 211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection parts of electrodes
218, 219 masking element
218A distal surface of masking element
218B proximal surface of masking element
220, 220A, 220B electrode configuration
222 ground electrode
222A ground connection part
222B ground sensing part
222C ground connector part
224 first electrode
224A first connection part
224B first sensing part
224C first conductor part
226 second electrode
226A second connection part
226B second sensing part
226C second conductor part
228 third electrode
228A third connection part
228B third sensing part
228C third conductor part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal 284 first terminal element
284A first terminal
286 second terminal element
286A second terminal
288 third terminal element
288A third terminal
290 fourth terminal element
290A fourth terminal
292 fifth terminal element
292A fifth terminal
301 memory
302 processor
303 interface
303a display
303b transceiver unit
400 first user interface
402 first user interface object
501 memory
502 one or more processors
503 interface
2104 curve showing a function of time, a diameter of the white ring of a base plate of the first type measured from a cut for a stomal opening to the first electrode pair
2102 a linear approximation of curve 2104
2106 curve showing, as function of time, a diameter of the white ring of a base plate of the first type measured from the first electrode pair to the second electrode pair
2108 a linear approximation of curve 2106
2110 a linear approximation of curve 2112
2112 curve showing, as function of time, a diameter of the white ring of a base plate of the second type measured from a cut for a stomal opening to the first electrode pair
2114 curve showing, as a function of time, a diameter of the white ring of a base plate of the second type measured from the first electrode pair to the second electrode pair
2116 a linear approximation of curve 2114

The invention claimed is:

1. An accessory device for an ostomy system comprising a monitor device and an ostomy appliance, the ostomy appliance comprising a base plate, the accessory device comprising:

a memory;
a processor; and
an interface coupled to the processor and configured to communicate with the monitor device, wherein the interface comprises a display and is configured to obtain monitor data from the monitor device coupled to the ostomy appliance,
wherein the processor is configured to:
obtain a base plate identifier from the base plate;
generate a request, to a server device, comprising the base plate identifier obtained from the base plate, for one or more base plate parameters including a first base plate parameter corresponding to a physical characteristic of a set of base plates that are each associated with the base plate identifier;
receive, from the server device in response to the request, the one or more base plate parameters associated with the base plate identifier;
process, by the accessory device, the monitor data from the monitor device to determine an operating state of the base plate based on the first base plate parameter obtained from the server device, thereby interpreting the monitor data according to the physical characteristic of the base plate as indicated by the first base plate parameter; and
display, on the display, a first user interface comprising a first user interface object representing the operating state of the base plate.

2. The accessory device according to claim 1, wherein the interface of the accessory device further comprises a transceiver unit, and wherein the request is transmitted and the one or more base plate parameters are received via the transceiver unit.

3. The accessory device according to claim 2, wherein:
the request comprises accessory data comprising the monitor data; and
the one or more base plate parameters of the base plate is further based on the monitor data.

4. The accessory device according to claim 1, wherein to determine an operating state of the base plate based on the first base plate parameter and the monitor data comprises to determine an estimate of remaining wear time of the base plate, and wherein the first user interface object represents the estimate of remaining wear time of the base plate.

5. The accessory device according to claim 1, wherein the monitor data comprises ostomy data obtained from electrodes of the base plate.

6. The accessory device according to claim 1, wherein the monitor data comprises parameter data based on ostomy data from electrodes of the base plate.

7. The accessory device of claim 1, wherein determining the operating state comprises transforming the monitor data according to the first base plate parameter.

8. The accessory device of claim 1, wherein criteria associated with the base plate identifier, as indicated by the one or more base plate parameters, are used to process the monitor data to determine the operating state.

9. The accessory device of claim 1, wherein the base plate identifier comprises a batch identifier for the set of base plates that are each associated with the base plate identifier.

10. A server device for an ostomy system comprising a monitor device, an ostomy appliance, and an accessory device, the ostomy appliance comprising a base plate, the server device comprising:

a memory;
one or more processors; and
an interface coupled to the one or more processors and configured to communicate with the accessory device,
wherein the one or more processors are configured to:
obtain, from a plurality of accessory devices by the server device, accessory data associated with a plurality of base plates having a base plate identifier;
process the accessory data from the plurality of accessory devices to generate a first base plate parameter corresponding to a physical characteristic of the plurality of base plates;
store, at the server device, the generated first base plate parameter in association with the base plate identifier;
receive, from the accessory device, a request for a base plate parameter, wherein the request comprises an indication of the base plate identifier; and
transmit, based on the association between the base plate identifier indicated by the request and the first base plate parameter generated for the plurality of accessory devices, the first base plate parameter to the accessory device in response to the request.

11. The server device according to claim 10, wherein the accessory data from the set of accessory devices comprises monitor data from monitor devices.

12. The server device according to claim 11, wherein the monitor data comprises ostomy data obtained from electrodes of the plurality of base plates.

13. The server device according to claim 11, wherein the monitor data comprises parameter data based on ostomy data from electrodes of the plurality of base plates.

14. The server device of claim 10, wherein the base plate identifier is a first base plate identifier and the one or more processors are further configured to:

receive, from a second accessory device, a request for a second base plate parameter, wherein the request comprises an indication of a second base plate identifier different than the first base plate identifier; and determine, based on the second base plate identifier, a second base plate parameter associated with the second base plate identifier, wherein the second base plate parameter is different than the first base plate parameter.

15. A method for adapting monitor data of a base plate based on a set of accessory devices, comprising:

obtaining, by an accessory device, a base plate identifier from the base plate;

requesting, from a server device, one or more base plate parameters for the base plate based on the base plate identifier, the one or more base plate parameters including a first base plate parameter corresponding to a physical characteristic of a set of base plates that are each associated with the base plate identifier;

receiving, from the server device in response to the request, the one or more base plate parameters associated with the base plate identifier;

processing, by the accessory device, the monitor data to determine an operating state of the base plate based on the first base plate parameter obtained from the server device, thereby interpreting the monitor data according to the physical characteristic of the base plate as indicated by the first base plate parameter; and displaying, on a display of the accessory device, a first user interface comprising a first user interface object representing the determined operating state of the base plate.

16. The method of claim 15, wherein determining the operating state comprises transforming the monitor data according to the first base plate parameter.

17. The method of claim 16, wherein requesting the one or more base plate parameters comprises transmitting the base plate identifier to the server device.

18. The method of claim 17, wherein:

requesting the one or more base plate parameters of the base plate comprises transmitting accessory data comprising the monitor data to the server device; and the one or more base plate parameters of the base plate is based on the monitor data.

19. The method of claim 16, wherein:

determining the operating state of the base plate comprises determining an estimate of remaining wear time of the base plate; and the first user interface object represents the estimate of remaining wear time of the base plate.

20. The method of claim 16, wherein the monitor data comprises at least one of:

ostomy data obtained from electrodes of the base plate; or parameter data based on ostomy data from electrodes of the base plate.

* * * * *